(12) United States Patent
Morris et al.

(10) Patent No.: US 9,381,093 B1
(45) Date of Patent: *Jul. 5, 2016

(54) LOCKING DEVICE FOR FIXATION MECHANISM OF MEDICAL IMPLANT

(71) Applicant: Alliance Partners, LLC, San Antonio, TX (US)

(72) Inventors: Frankie Morris, Austin, TX (US); Mike Faraj, San Antonio, TX (US); Justin Rice, San Antonio, TX (US)

(73) Assignee: Alliance Partners, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,913

(22) Filed: Mar. 10, 2015

Related U.S. Application Data

(63) Continuation of application No. 14/617,401, filed on Feb. 9, 2015, now abandoned.

(51) Int. Cl.
*A61F 2/44* (2006.01)

(52) U.S. Cl.
CPC ....... *A61F 2/4455* (2013.01); *A61F 2220/0016* (2013.01)

(58) Field of Classification Search
CPC .................. A61B 17/8047; A61B 17/8042
USPC .............. 411/81, 84, 389; 606/289, 290, 293, 606/294, 295, 296
See application file for complete search history.

(56) References Cited

U.S. PATENT DOCUMENTS

| | | | |
|---|---|---|---|
| 5,951,558 A | 9/1999 | Fiz | |
| 6,152,927 A | 11/2000 | Farris et al. | |
| 6,193,721 B1 | 2/2001 | Michelson | |
| 6,235,059 B1 * | 5/2001 | Benezech et al. | 623/17.16 |
| 6,258,089 B1 | 7/2001 | Campbell et al. | |
| 7,004,944 B2 * | 2/2006 | Gause | 606/294 |
| 8,454,667 B2 | 6/2013 | Humphreys | |
| 8,641,768 B2 | 2/2014 | Duffield et al. | |
| 8,652,182 B1 | 2/2014 | Walker et al. | |
| 8,702,766 B2 | 4/2014 | Mueller | |
| 8,821,553 B2 | 9/2014 | Kirschman | |
| 8,932,335 B2 | 1/2015 | Humphreys | |
| 2002/0004683 A1 * | 1/2002 | Michelson | 623/17.16 |
| 2002/0120272 A1 * | 8/2002 | Yuan et al. | 606/61 |
| 2002/0147450 A1 | 10/2002 | LeHuec et al. | |
| 2003/0040749 A1 | 2/2003 | Grabowski et al. | |
| 2003/0060828 A1 * | 3/2003 | Michelson | 606/71 |
| 2004/0015169 A1 | 1/2004 | Gause | |
| 2005/0059971 A1 * | 3/2005 | Michelson | 606/69 |

(Continued)

OTHER PUBLICATIONS

Surgical Technique Guide, Trestle Anterior Cervical Plating System, Alphatec Spine, 2010, 16 pages.

(Continued)

*Primary Examiner* — Jan Christopher Merene
(74) *Attorney, Agent, or Firm* — Greenberg Traurig, LLP; Ross Spencer Garsson

(57) ABSTRACT

A device for locking a bone fastening or fixation mechanism in a receiving member of a medical implant (corpectomy cage or cervical cage). The locking mechanism is kept in place (both in its locked and unlocked positions) using a retaining mechanism. The retaining mechanism also provides predetermined locked and unlocked positions that are readily moved to by the practitioner and maintained in position once placed there.

28 Claims, 28 Drawing Sheets

(56) References Cited

U.S. PATENT DOCUMENTS

| | | |
|---|---|---|
| 2005/0075633 A1 | 4/2005 | Ross |
| 2007/0213728 A1* | 9/2007 | Lindemann et al. ............ 606/69 |
| 2008/0097444 A1 | 4/2008 | Erickson et al. |
| 2008/0177307 A1* | 7/2008 | Moskowitz et al. .......... 606/246 |
| 2009/0105831 A1* | 4/2009 | Jones et al. ................ 623/17.16 |
| 2010/0057206 A1* | 3/2010 | Duffield et al. ........... 623/17.16 |
| 2010/0305704 A1* | 12/2010 | Messerli et al. ........... 623/17.16 |
| 2011/0166658 A1* | 7/2011 | Garber et al. .............. 623/17.16 |
| 2012/0158068 A1* | 6/2012 | Humphreys .................. 606/286 |
| 2013/0253655 A1* | 9/2013 | Blain ......................... 623/17.16 |

OTHER PUBLICATIONS

Fortify I-R, Fortify I-R Spacer Corpectomy Spacer System, Globus Medical, 2014, 2 pages.

Trinica and Trinica Select Anterior Cevical Plate System, Zimmer, Inc., 2014, 2 pages.

* cited by examiner

LOCKING DEVICE FOR FIXATION MECHANISM OF MEDICAL IMPLANT

CROSS-REFERENCE TO RELATED PATENT APPLICATIONS

This application is a continuation of U.S. patent application Ser. No. 14/617,401 filed on Feb. 9, 2015, entitled "Locking Device For Fixation Mechanism Of Medical Implant" (now abandoned). This application is also related to, but does not claim the benefit of, co-pending U.S. patent application Ser. No. 14/643,881, filed on Mar. 10, 2015, which is a continuation of U.S. patent application Ser. No. 14/617,367, filed Feb. 9, 2015, entitled "Locking Device For Fixation Mechanism Of Medical Implant," (now abandoned). These applications are commonly assigned to the Assignee of the present invention and are hereby incorporated herein by reference in their entirety for all purposes.

FIELD OF INVENTION

A device for locking a bone fastening or fixation mechanism in a receiving member of a medical implant.

BACKGROUND OF INVENTION

The spine is the axis of the skeleton on which all of the body parts hang. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation and translation.

Typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

The success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth.

Corpectomy cages have been developed to help support the spine and maintain the normal spacing between opposing vertebrae. Typically, corpectomy cages are pre-manufactured at various heights requiring that a cavity between opposing vertebrae be prepared and distracted to a dimension corresponding to the most suitably sized corpectomy cage. The surgical procedure to prepare the implant site can be difficult and lengthy. Moreover, the procedure can increase risk of trauma to the tissues surrounding of the implant site.

Distractible corpectomy cages may be used as both a fusion device and/or a means for maintaining intervertebral spacing. Often these implants include a drive means that allows the corpectomy cage to be expanded in situ to a size that corresponds to the cavity created when the damaged tissue is removed. The drive means typically includes devices such as gears, threaded rods, and the like, in mechanical engagement so as to expand or contract the device to a necessary distance between the vertebrae.

Cervical cages are also used to stabilize the spine during the fusion process. These devices likewise include one or more plates and fasteners (typically screws) for aligning and holding vertebrae in a fixed position with respect to one another.

A common failure for corpectomy cages and cervical cages is the backing out of screws into soft tissues of the patient's body. The backing out of the screws is typically a result of the screws failure to achieve a sufficient purchase in the bone, although the stripping of the screws has also been known to cause this problem. Another common problem is that these devices require "carpentry" work to match fit aspects of the vertebral bodies.

Thus, it is important that the medical implant (corpectomy cage or cervical cage) is properly held in place by the fastener. To keep the fastener from backing out, a locking device is typically utilized. The locking device physically impedes the top of the screw from rising, which prevents the fastener from rotating (as this would cause the fastener to rise). Once the locking device is in the "locked" position, the fixation mechanism is held in place.

It is further important that the locking device be properly positionable both in the unlocked position (so that the medical practitioner can have access to properly position and implant the fastener) and the locked position (so that the locking device can properly function). Accordingly, there is a need for an improved locking device for corpectomy cages and cervical cages.

SUMMARY OF INVENTION

The present invention is a medical implant (corpectomy cage or cervical cage) that is held in place by a fixation mechanism, that is, typically, a screw. To keep the screw from backing out, a locking device is utilized. The locking device physically impedes the top of the screw from rising, which prevents the screw from rotating (as this would cause the screw to rise). The locking device has a retention device that controllably maintains the locking device in the unlocked and locked positions as the case may be. The retention device provides for hard stops for the locking device in its unlocked and locked positions, while maintaining a low profile.

In general, in one aspect, the invention features a medical implant that includes a receiving member body that has a first fastener opening. The first fastener opening is operable for allowing a first fastener to be inserted through the first fastener opening for fixing the medical implant to bone. The medical implant further has a locking mechanism located near the first fastener opening. The locking mechanism includes a rotating block cover operable to move between an unlocked position and a locked position. When the rotating block cover is in the unlocked position, the first fastener can be inserted through the first fastening opening. When the rotating block cover is in the locked position, a portion of the rotating block cover is covering the first fastener opening to prevent the first fastener for moving through the first fastener opening and which locks the first fastener in place. The medical implant further includes a retaining mechanism that has an engagement body rotatably coupled to at least two retaining levers. The engagement body is attached to the rotating block cover. The engagement body is operable for moving rotatably through the retaining levers. The engagement body is operable for moving in a first direction to a first position. When the engagement body is in the first position, the locking mechanism is in the unlocked position. The engagement body is blocked from rotating past the first position when moved in the first direction. The engagement body is retained in the first position by the retaining levers such that the engagement body cannot move without the application of a force in a second direction that is opposite to the first direction. The engagement body is operable for moving in a second direction to a second position. When the engagement body is in the second position, the locking mechanism is in the locked position. The engagement body is blocked from rotating past the second position when moved in the second direction. The engagement body is retained in the second position by the retaining levers such that the engagement body cannot move without the application of a force in the first direction. The medical implant is a cage.

Implementations of the invention can include one or more of the following features:

The medical implant can be a corpectomy cage.

The medical implant can be a cervical cage.

The medical implant can further include a second fastener opening. The second fastener opening can be operable for allowing a second fastener to be inserted through the second fastener opening for fixing the medical implant to bone. The locking mechanism can further be located near the second fastener opening. When the rotating block cover is in the unlocked position, the second fastener can be inserted through the second fastening opening. When the rotating block cover is in the locked position, a portion of the rotating block cover can be covering the second fastener opening to prevent the second fastener for moving through the second fastener opening and which locks the second fastener in place.

The first fastener can include a bone screw.

The retaining mechanism can include exactly two retaining levers.

Each of the retaining levels can have an indent that retains the engagement body in the first position and the second position.

The rotating block cover can have a hole operable for receiving a rotatable tool. The rotating block cover can be rotatable in the first direction and the second direction using the rotating tool.

The receiving member body can include a plurality of fastener openings and plurality of locking mechanisms. Each of the locking mechanisms can be operable for locking fasteners positioned in at most two of the fastener openings.

Each of the locking mechanisms can be operable for locking fasteners positioned in at most one of the fastener openings.

The medical implant can be a single-part medical implant. The single part can include titanium.

The medical implant can be a two-part medical implant including a first part and a second part. The first part can include titanium. The second part can include a biocompatible polymer.

The biocompatible polymer can be polyether ether ketone (PEEK).

In general, in another aspect, the invention features a method of locking and unlocking a fastener used to fix a medical implant. The method includes selecting a medical implant having a receiving body that includes a first fastener opening, a locking mechanism, and a retaining mechanism. The locking mechanism includes a rotating block cover operable to move between an unlocked position and a locked position. The locking mechanism is in the unlocked position. The retaining mechanism includes an engagement body rotatably coupled to at least two retaining levers. The engagement body is attached to the rotating block cover. The retaining mechanism retains the engagement body at a first position to maintain the rotating block cover in the unlocked position. The method further includes inserting a first fastener into the first fastener opening. The method further includes securing the first fastener to a bone. The method further includes rotating the locking mechanism from the unlocked position to the locked position. A portion of the rotating block cover is covering the first fastener opening to prevent the first fastener for moving through the first fastener opening and which locks the first fastener in place. The engagement body is blocked from rotating to prevent the rotating lock cover from rotating past the locked position. The retaining mechanism retains the engagement body at second position to maintain the rotating block cover in the locked position. The medical implant is a cage.

Implementations of the invention can include one or more of the following features:

The medical implant can be a corpectomy cage.

The medical implant can be a cervical cage.

The medical implant can further include a second fastener opening. The method can further include inserting a second fastener into the second fastener opening. The method can further include securing the second fastener to the bone while the locking mechanism is in the unlocked position. The step of rotating the locking mechanism can further include that a portion of the rotating block cover is covering the second fastener opening to prevent the second fastener for moving through the second fastener opening and which locks the second fastener in place.

The first fastener can include a bone screw.

The retaining mechanism can include exactly two retaining levers.

Each of the retaining levels can have an indent that retains the engagement body in the first position and the second position.

The step of rotating the locking mechanism can include inserting a rotating tool into a hole in the rotating block cover and rotating the rotating tool.

The receiving member body can include a plurality of fastener openings and plurality of locking mechanisms. The method can further include moving each of the locking mechanisms in the plurality of locking mechanism to lock at most two fasteners positioned in at most two fastener openings.

The method can further include moving each of the locking mechanisms in the plurality of locking mechanism to lock at most one fastener.

The medical implant can be a single-part medical implant. The single part can include titanium.

The medical implant can be a two-part medical implant including a first part and a second part. The first part can include titanium. The second part can include a biocompatible polymer.

The biocompatible polymer can be PEEK.

The method can further include rotating the locking mechanism from the locked position to the unlocked position. No portion of the rotating block cover can be covering the first fastener opening which unlocks the first fastener. The engagement body can be blocked from rotating to prevent the rotating lock cover from rotating past the unlocked position. The retaining mechanism can retain the engagement body at the first position to maintain the rotating block cover in the unlocked position.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

It is also to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

The technology relates to a device for locking a bone fastening or fixation mechanism in a receiving member of a medical implant. The bone fastening or fixation mechanism is used to mount the receiving member to a bone structure in the medical implant. The locking mechanism prevents the bone fastening mechanism for backing out of the receiving member. A retention mechanism is used to controllable move and retain the locking mechanism in the locked (closed) or unlocked (open) position.

Figure 1A:
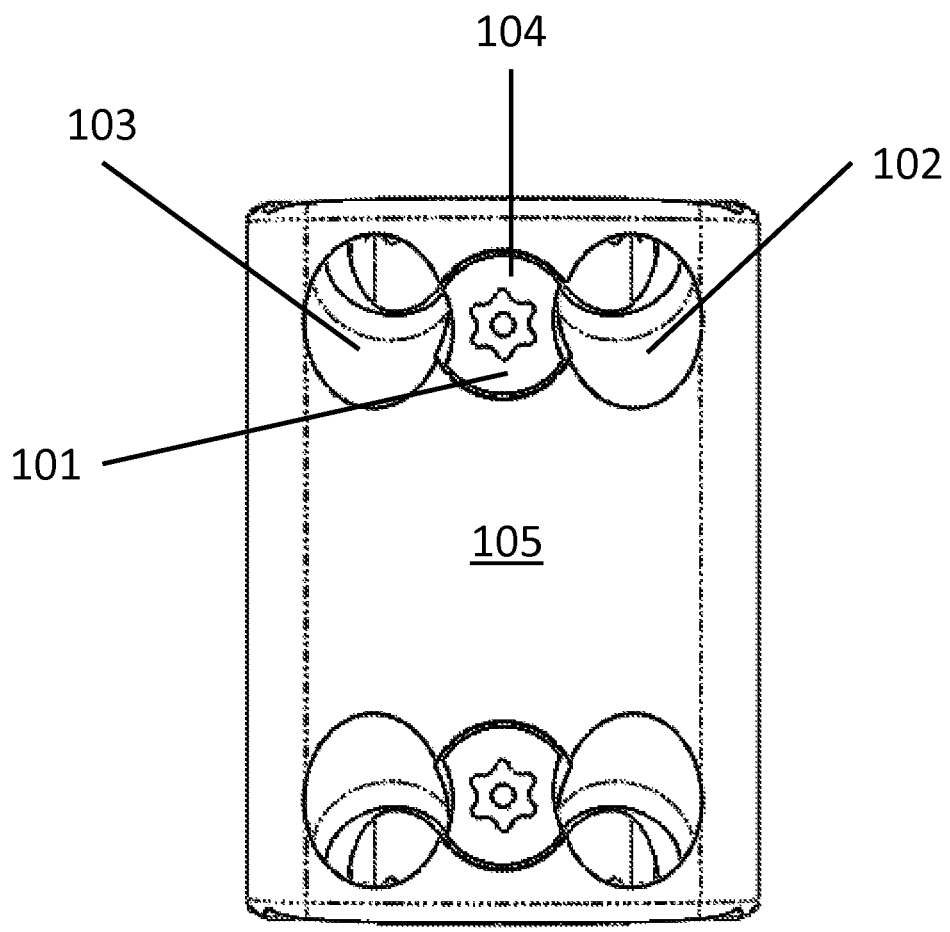
FIG. 1A is a front view of an embodiment of the present invention showing a two-part corpectomy cage with the locking mechanism in the unlocked position.
Figure 1B:
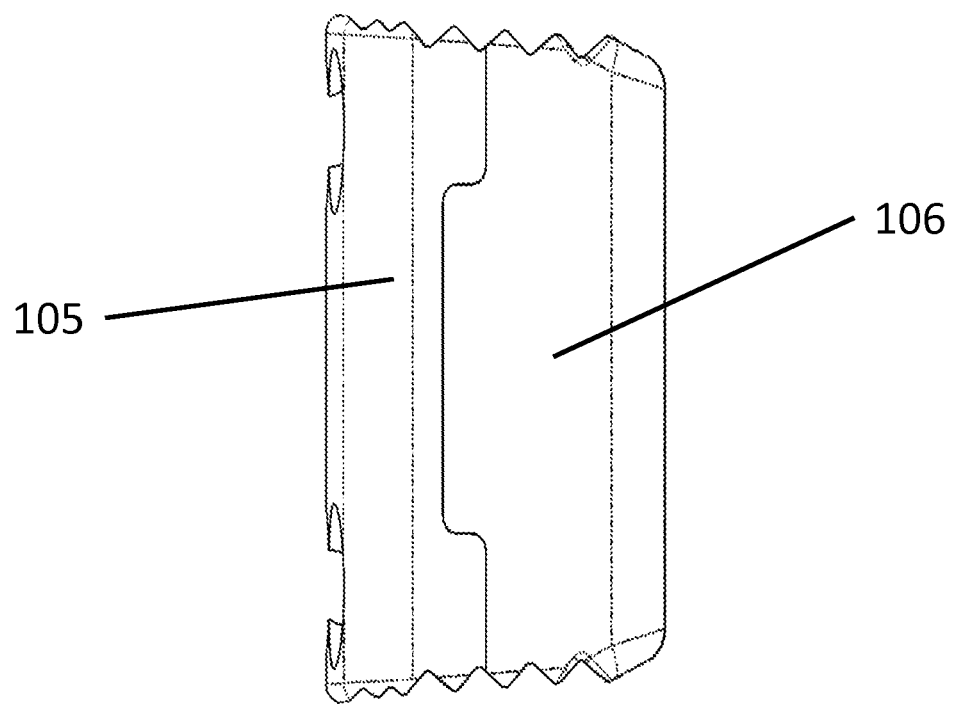
FIG. 1B is a right view of the embodiment of FIG. 1A.
Figure 1C:
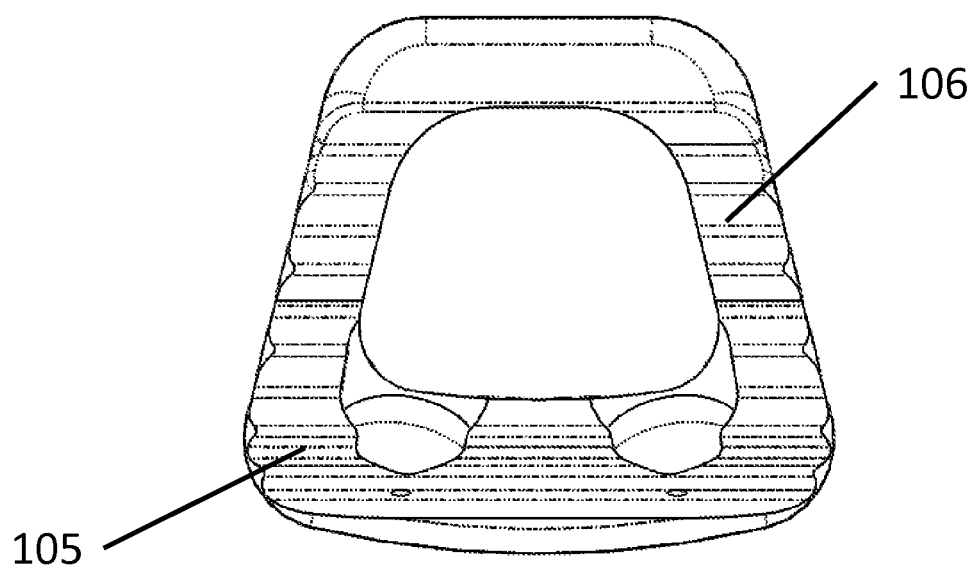
FIG. 1C is a top view of the embodiment of FIG. 1A.

Referring to the figures, FIG. 1A is a front view of an embodiment of the present invention showing a two-part corpectomy cage 100 with the locking mechanism 101 in the unlocked position. The locking mechanism 101 has a rotating blocker cover 701 (shown in more detail in FIGS. 7A-7D discussed below) that can be rotated to partially cover holes (bone screw holes) 102 and 103. (The holes are also referred to as "fastener openings") As shown in FIG. 1A, the locking mechanism 101 is in the unlocked (otherwise known as open) position in that fasteners (screws) can be fit through holes 102 and 103 for implantation to fasten the corpectomy cage 100. FIG. 1B is a right view of the corpectomy cage 100. FIG. 1B shows upper part 105 and lower part 106, which can be made from a biocompatible material. For instance, upper part 105 can be made of titanium, and lower part 106 can be made from PEEK or another biocompatible polymer. FIG. 1C is a top view of corpectomy cage 100.

Figure 2:
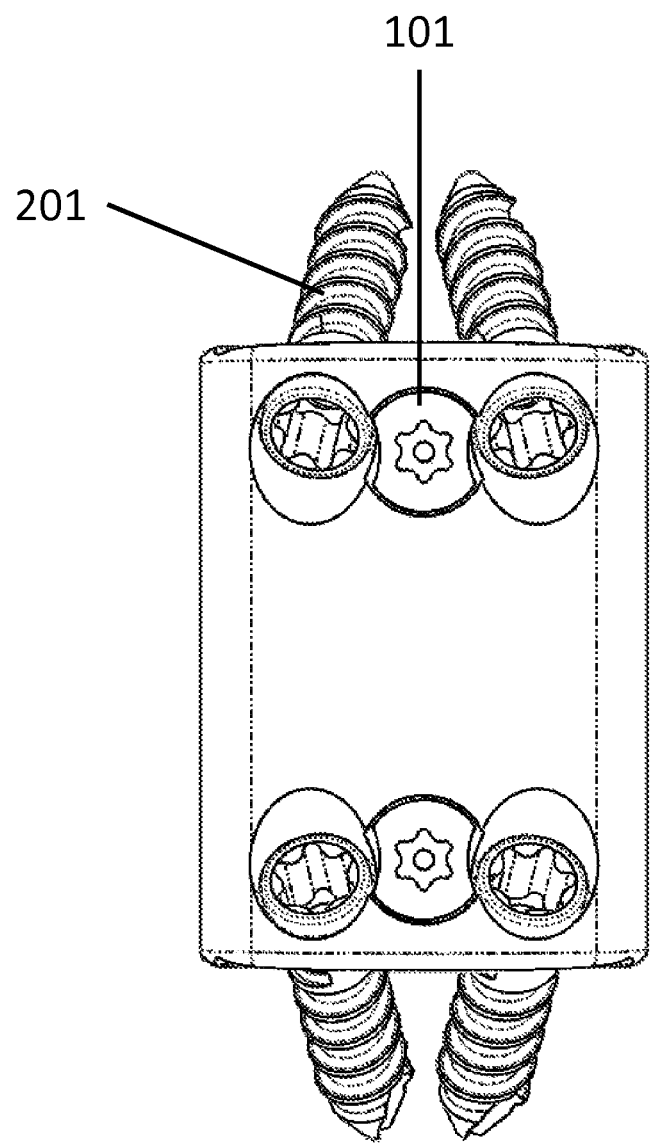
FIG. 2 is a front view of the embodiment of FIG. 1A with fasteners (screws) inserted within. The locking mechanism is in the unlocked position.
Figure 3:
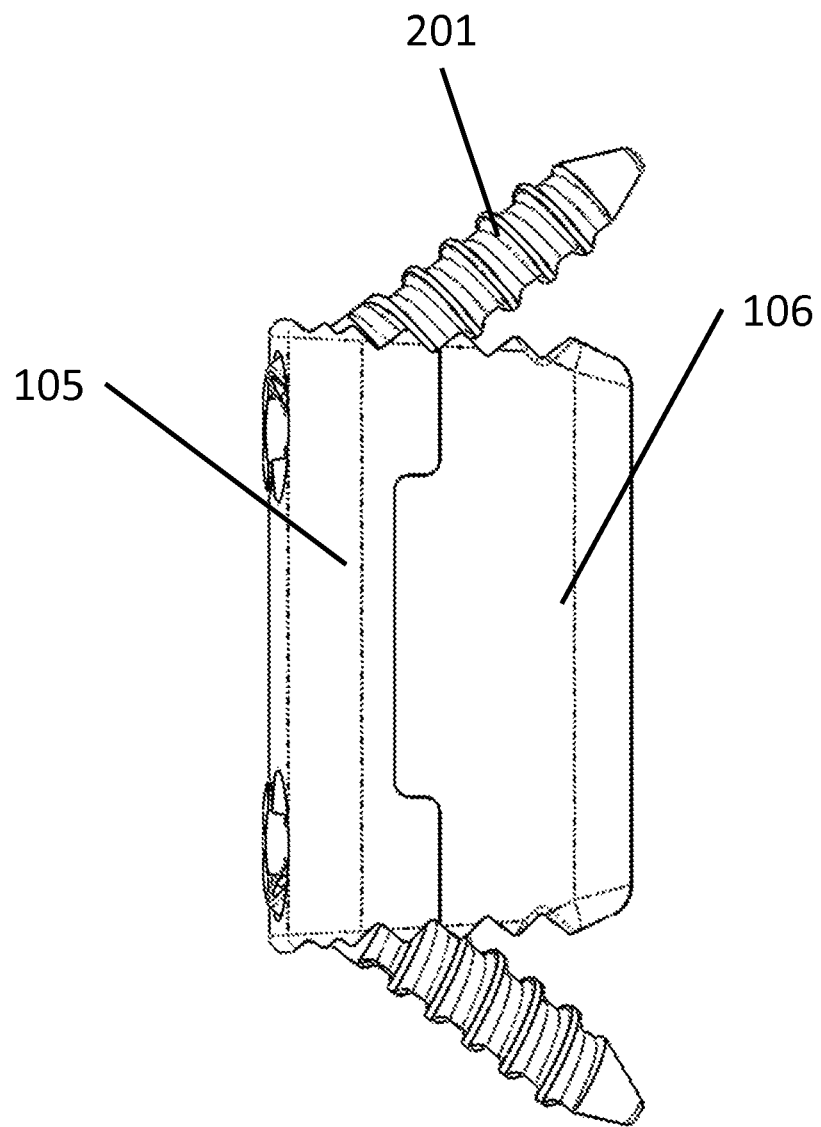
FIG. 3 is a right view of the embodiment of FIG. 2.
Figure 4:
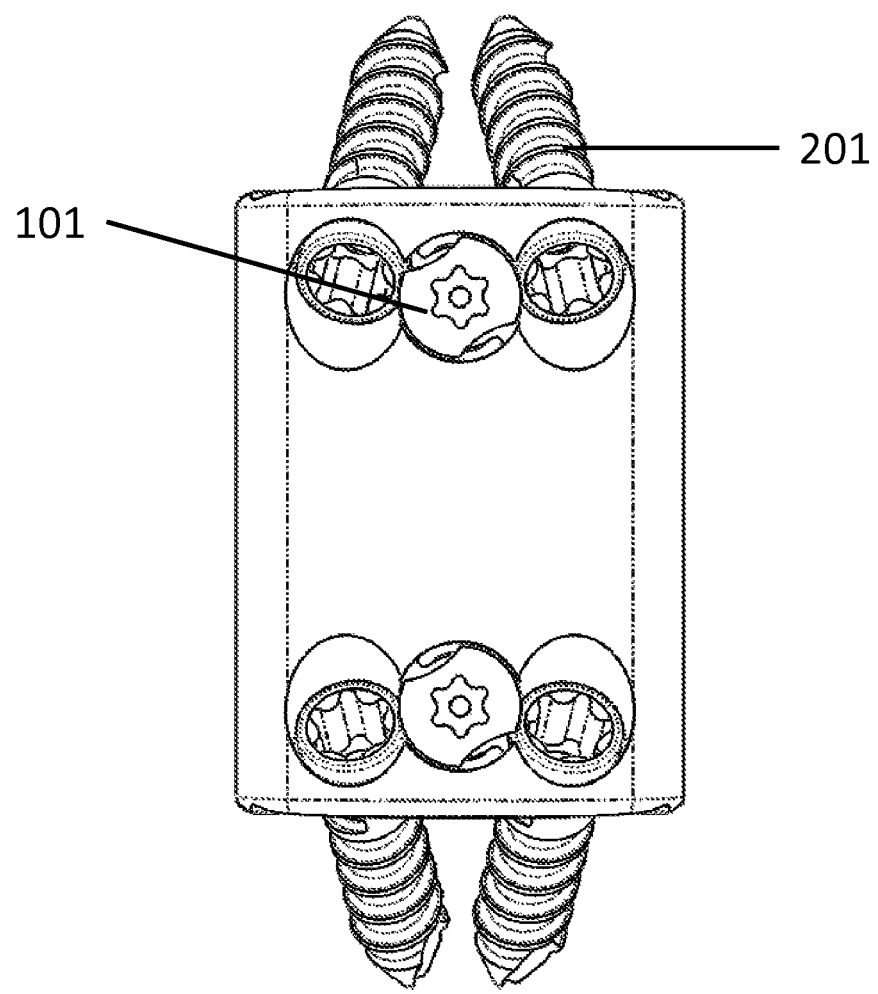
FIG. 4 is a front view of the embodiment of FIG. 2 with the locking mechanism in the locked position.

FIG. 2 is a front view of corpectomy cage 100 with fasteners 201 (bone screws) inserted within holes 102 and 103. FIG. 3 is a right view of corpectomy cage 100 with the fasteners 201 inserted. Such insertion of fasteners 201 can incur into holes 102 and 103 because rotating blocker cover 701 of locking mechanism 101 is in the open position. Locking mechanism 101 is rotatably connected to corpectomy cage 100. Locking mechanism 101 can be rotated using the star-shaped hole 104 that can be engaged with a rotatable tool. As shown in FIGS. 2 and 4, rotating locking mechanism 101 in the clockwise direction moves locking mechanism to the locked (otherwise known as closed) position. FIG. 4 is a front view of the embodiment of corpectomy cage 100 with the locking mechanism 101 in the locked position.

When locking mechanism 101 is in the locked position, the fastener 201 is blocked for moving upwards and out through holes 102 and 103. Because fastener 201 cannot move upward and out, the fastener 201 cannot itself rotate (as rotating would cause it to move upward and out). Such blocking occurs due to the shape of rotating blocker cover 701 which, when the locking mechanism 101 is rotated such that a portion of rotating blocker cover 701 overlays holes 102 and 103. Examples of locking mechanisms known in the art are shown in U.S. Pat. No. 8,702,766, issued Apr. 22, 2014 to Mueller and U.S. Pat. No. 8,641,768, issued Feb. 4, 2014, to Duffield et al.

Figure 5:
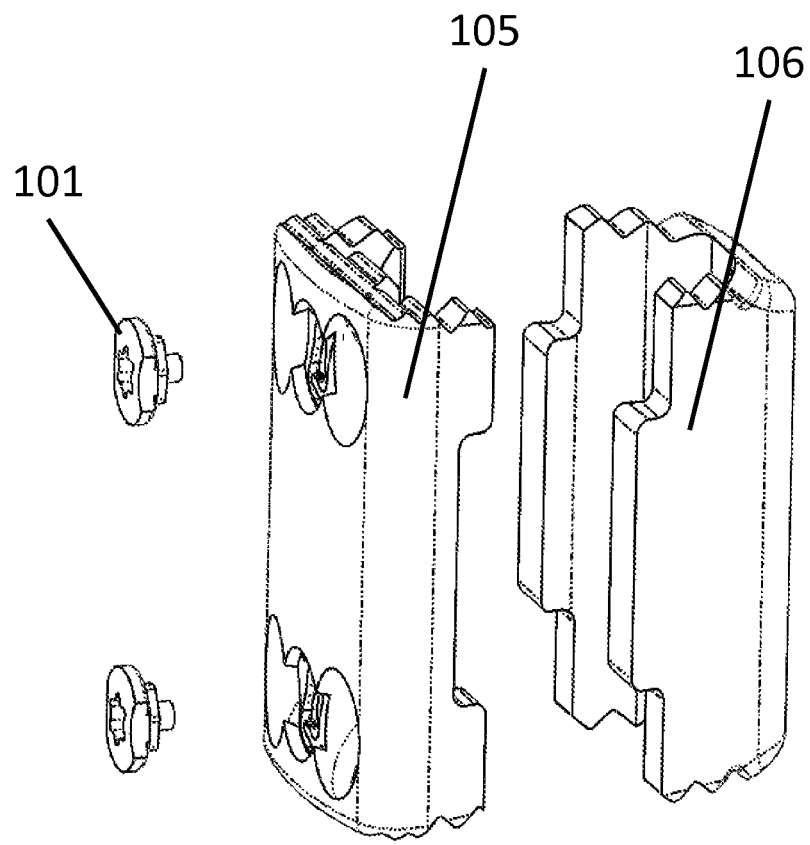
FIG. 5 is an exploded view of the embodiment of FIG. 1A.
Figure 6A:
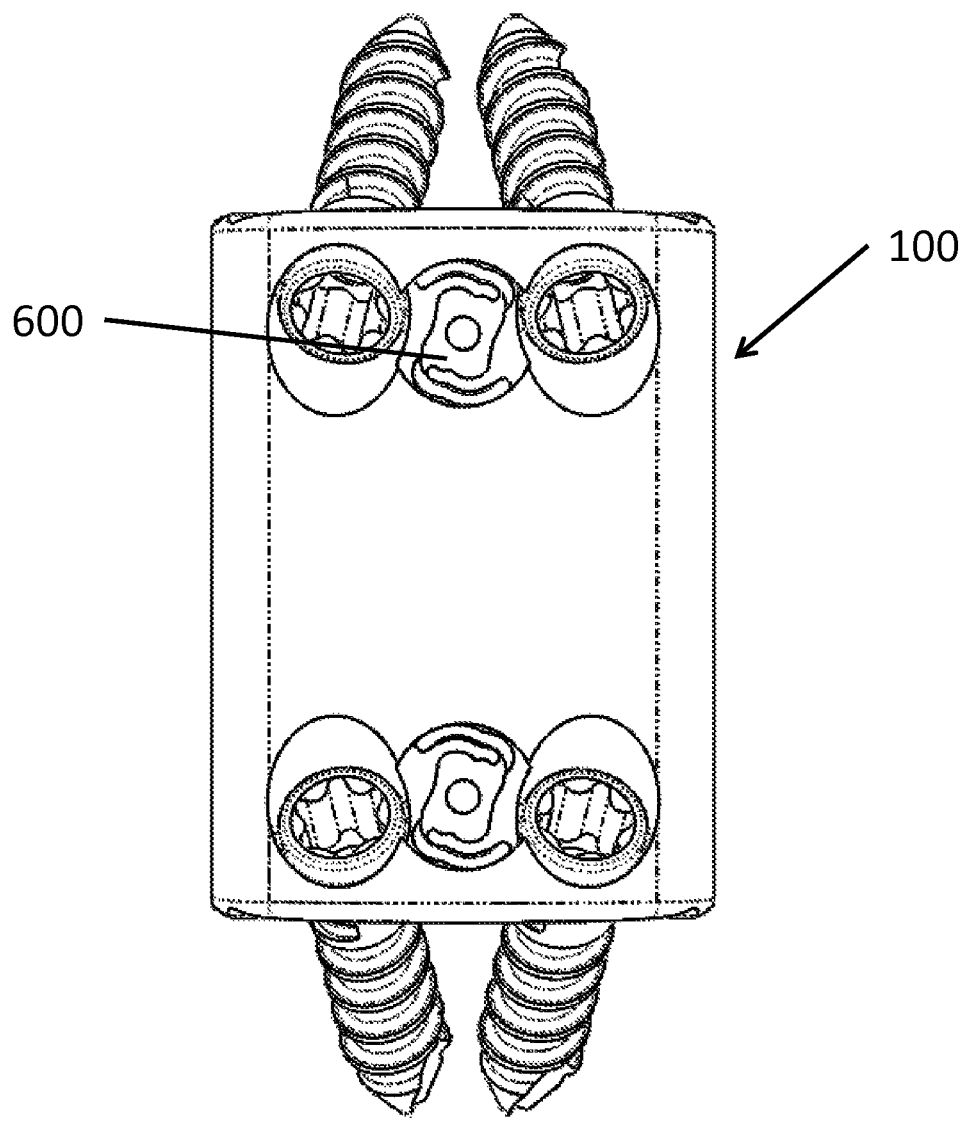
FIG. 6A is a front view of the embodiment of FIG. 1A with the locking mechanism removed to show the retaining mechanism.
Figure 6B:
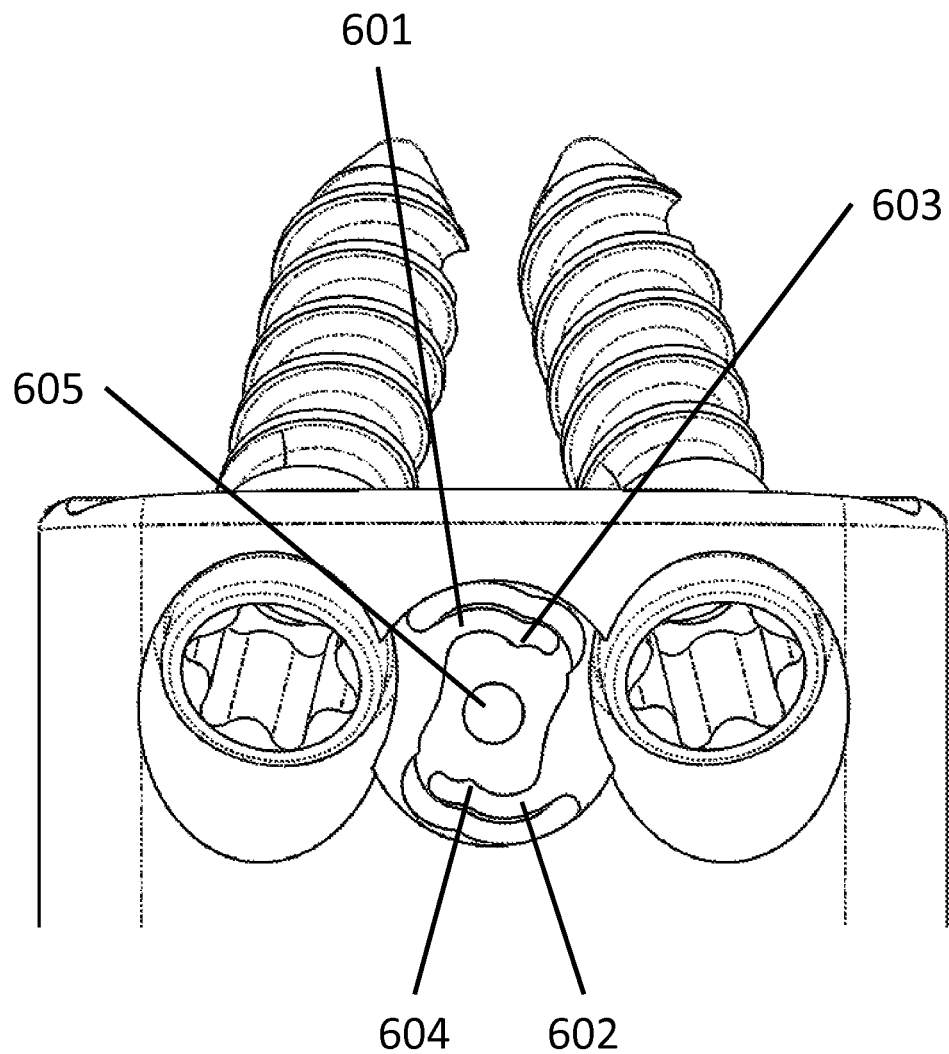
FIG. 6B is an enlarged front view of the retaining mechanism shown in FIG. 6A.

FIG. 5 is an exploded view of corpectomy cage 100 in which locking mechanism 101 has been separated from upper part 105 and lower part 106 of the corpectomy cage 100 to show the retaining mechanism that lies beneath. FIG. 6A is a front view of corpectomy cage 100 with the locking mechanism 101 removed to show the retaining mechanism 600. FIG. 6B is an enlarged front view of the retaining mechanism shown in FIG. 6A.

The retaining mechanism 600 has a pair of retaining levers (or arms) 601 and 602. Hole 605 is positioned within the retaining mechanism 600 and is where locking mechanism 101 (not shown) is rotatably connected to corpectomy cage 100. Each of retaining levers 601 and 602 has an indent 603 and 604, respectively, which is utilized in the retaining of the locking mechanism.

The retaining levers 601 and 602 oppose one another to apply a force to the locking mechanism 101 when retaining it in either the locked or unlocked position. The retaining levers 601 and 602 also control the rotational movement of the locking mechanism 101 such that it cannot be over rotated when moving from one position to the other.

Figure 7A:
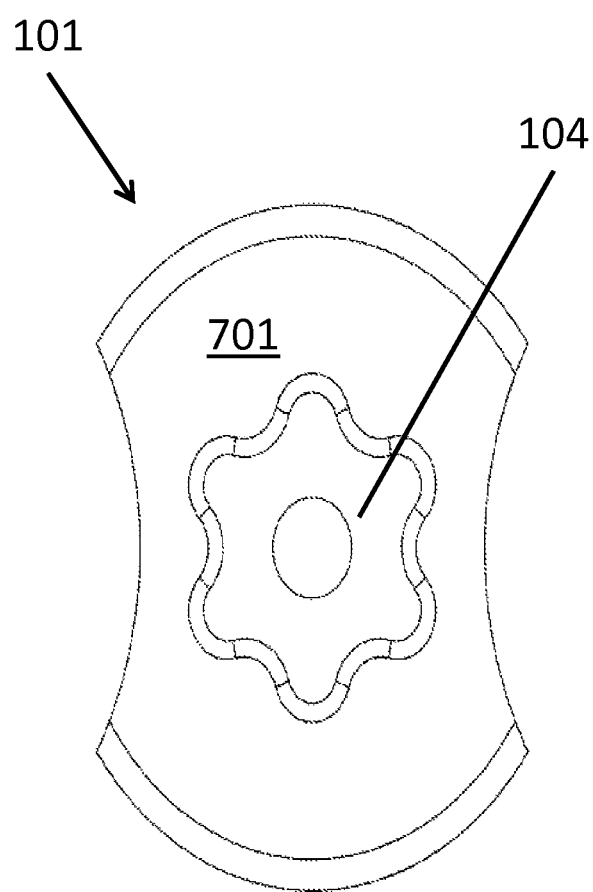
FIG. 7A is a top view of a locking mechanism used in embodiments of the invention.
Figure 7B:
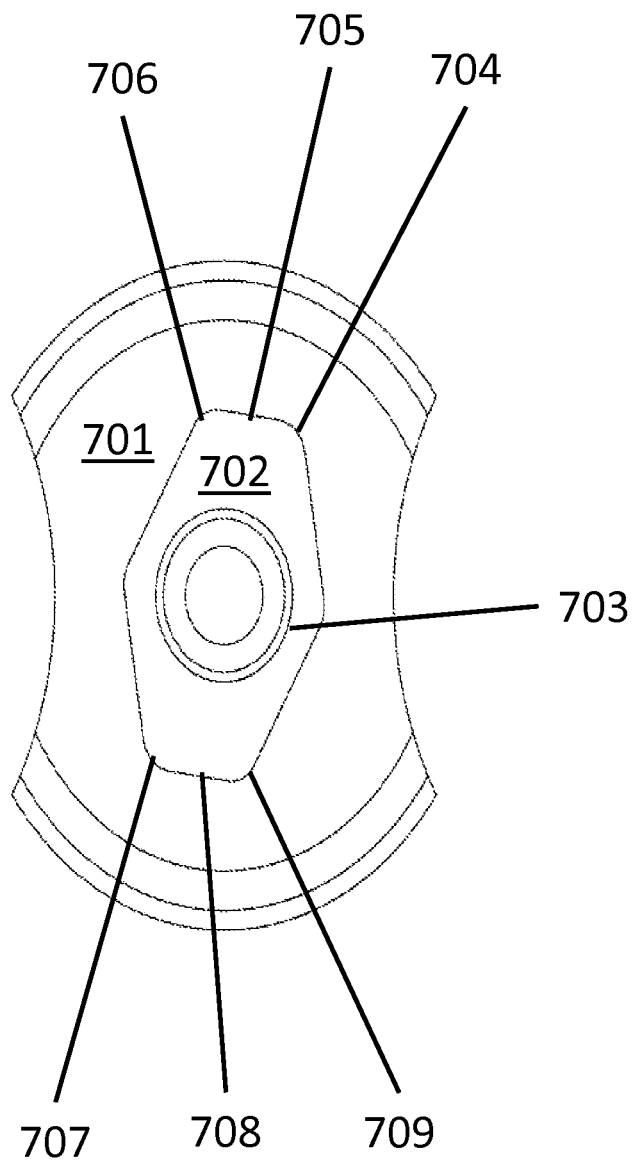
FIG. 7B is a bottom view of the locking mechanism shown in FIG. 7A.
Figure 7C:
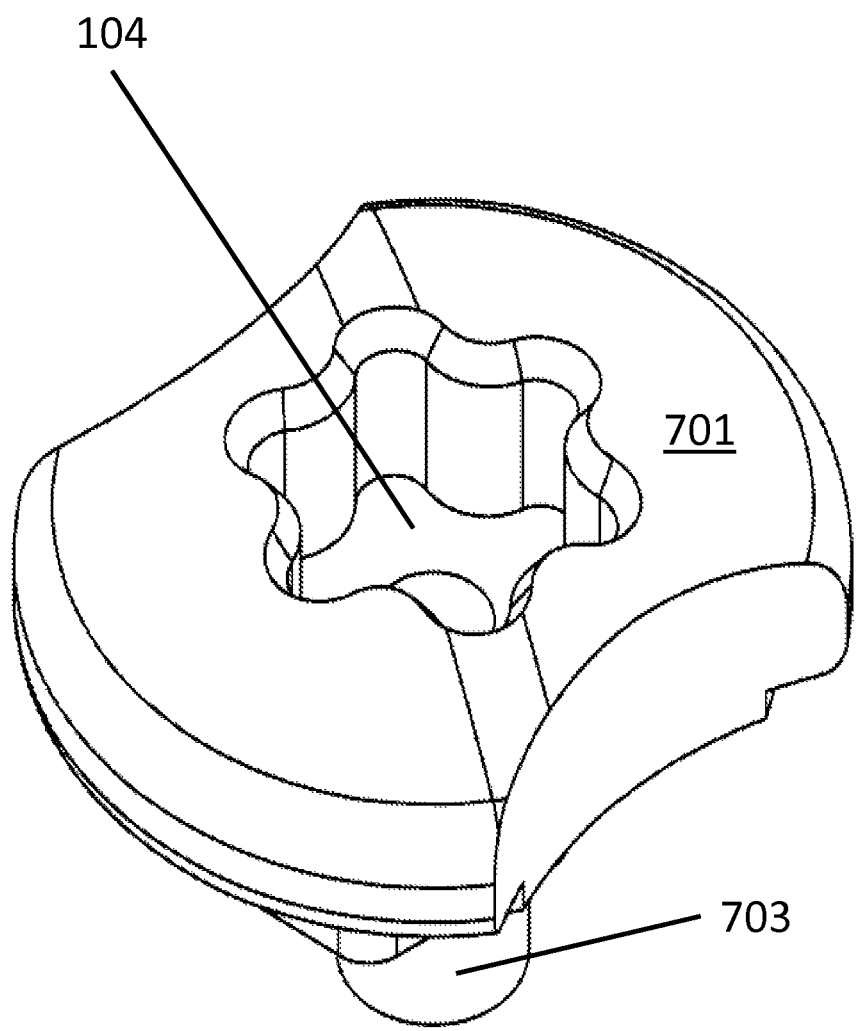
FIGS. 7C-7D are perspective views of the locking mechanism shown in FIG. 7A.
Figure 7D:
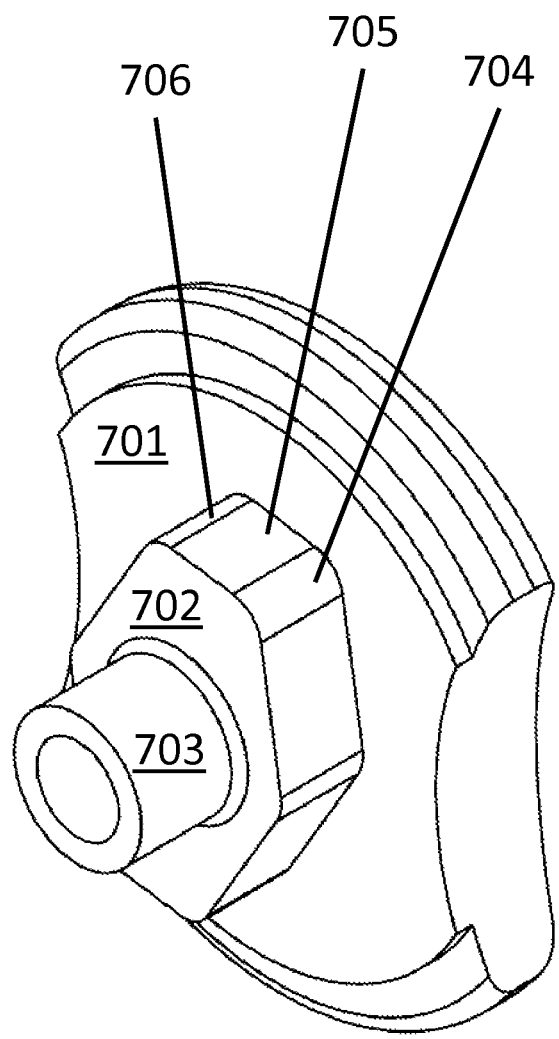

FIGS. 7A-7D are illustrations of locking mechanism 101. FIGS. 7A-7B are top and bottom views of locking mechanism 101. FIGS. 7C-7D are perspective view of locking mechanism 101. The locking mechanism 101 includes a rotating blocker cover 701, which is the portion of the locking mechanism 101 that, when rotated, will partially cover holes 102 and 103 when the locking mechanism is in the locked position.

Locking mechanism 101 has a post 703 that is rotatably connected within hole 605 (shown in FIG. 6B). Locking mechanism 101 further has an engagement body 702 that is engagable with retaining levers 601 and 602 to retain locking mechanism 101 in its locked and unlocked position, as the case may be. As shown in FIGS. 7B and 7D, engagement body 702 can be geometric shaped, such as the multisided shaped body shown in those figures. Engagement body 702 includes sides 704-709, which, when the locking mechanism 101 is in place, are positioned to engage with retaining levers 601 and 602 (and their respective indents 603 and 604).

Figure 8A:
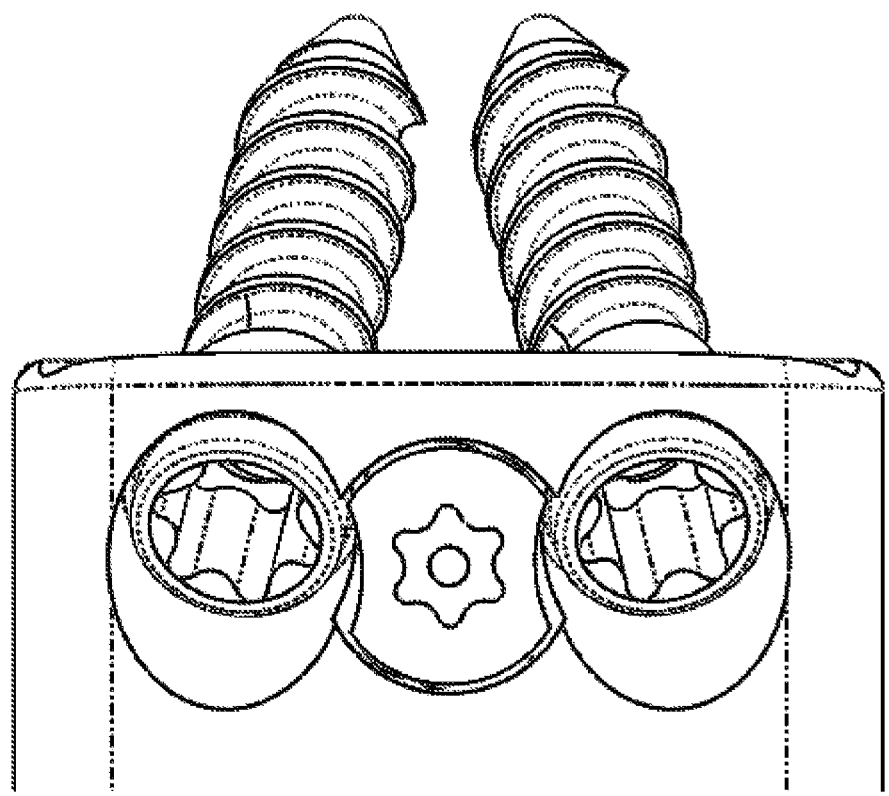
FIG. 8A is an enlarged front view of locking mechanism shown in FIG. 2.
Figure 8B:
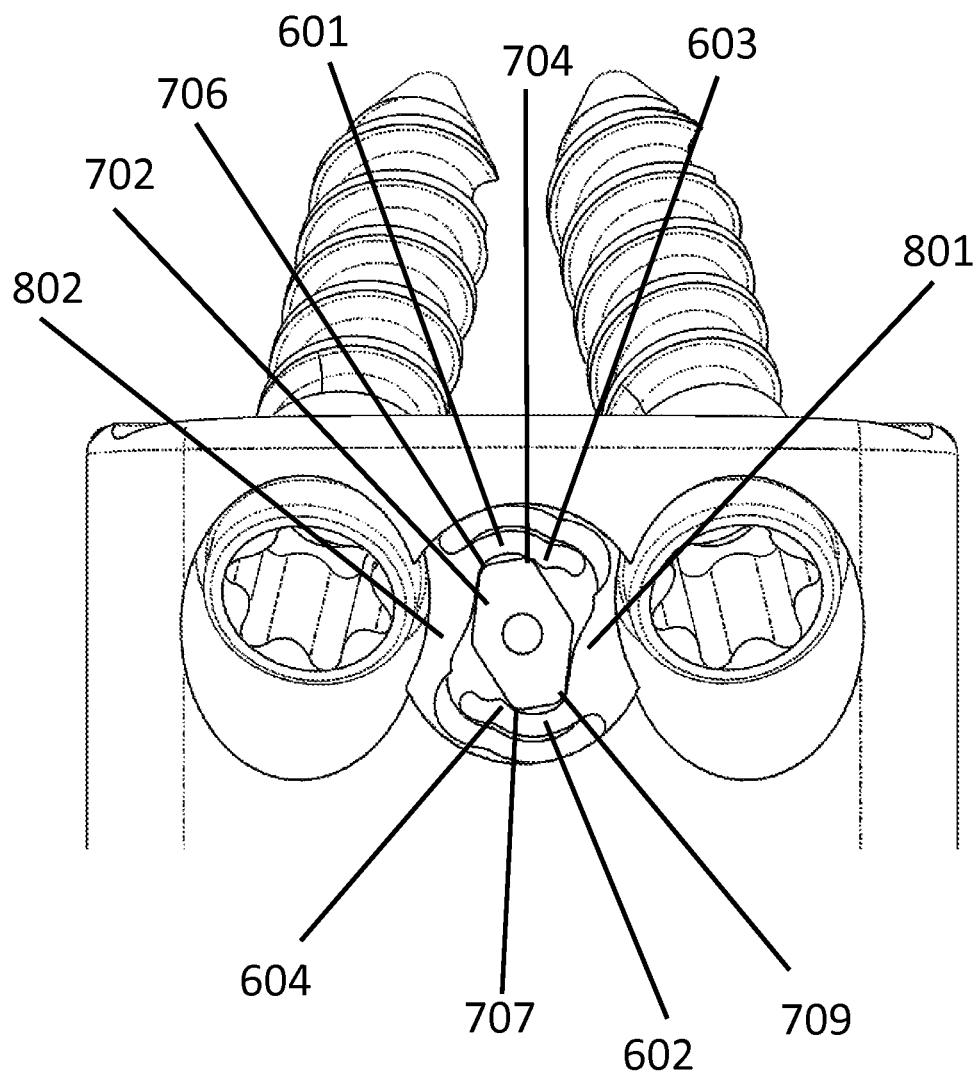
FIG. 8B is the enlarged front view of the locking mechanism shown in FIG. 8A without the cover piece of the locking mechanism.

FIGS. 8A-8B and 9A-9B illustrate the operability of the retaining mechanism 600 with respect to locking mechanism 101. FIG. 8A shows locking mechanism 101 in corpectomy cage 100 in the unlocked position. FIG. 8B is the same view as FIG. 8A, except without showing rotating blocker cover 701. This allows the underworking to be more readily viewed and described. As shown in FIG. 8B, engagement body 702 is positioned within retaining levers 601 and 602, such that sides 704 and 705 are nestled in place in retaining lever 601. As shown in FIG. 8B, indent 603 is to the immediate right of side 704, which maintains engagement body in this position and keeps engagement body 702 from rotating in the clockwise direction. Likewise, sides 706 and 708 are nestled in place in retaining lever 602, with indent 604 to the immediate left of side 707, and which likewise maintains engagement body in this position and keeps engagement body 702 from rotating in the clockwise direction. Thus, the engagement between the engagement body 702 and retaining levers 601 and 602 prevents engagement body 702 (and thus locking mechanism 101) from rotating clockwise into the locked position.

Furthermore, walls 801 and 802 block engagement body 702 from being able to rotate counter-clockwise (i.e., to rotate in the backwards direction). If that were not the case, then locking mechanism could rotate counter-clockwise into a locked position.

Accordingly, the engagement between the engagement body 702 and retaining levers 601 and 602 will maintain the locking mechanism in the unlocked position once positioned there. Moreover, as over-rotation is not possible, the practitioner using the corpectomy cage 100 will know that it has been properly positioned.

Figure 9A:
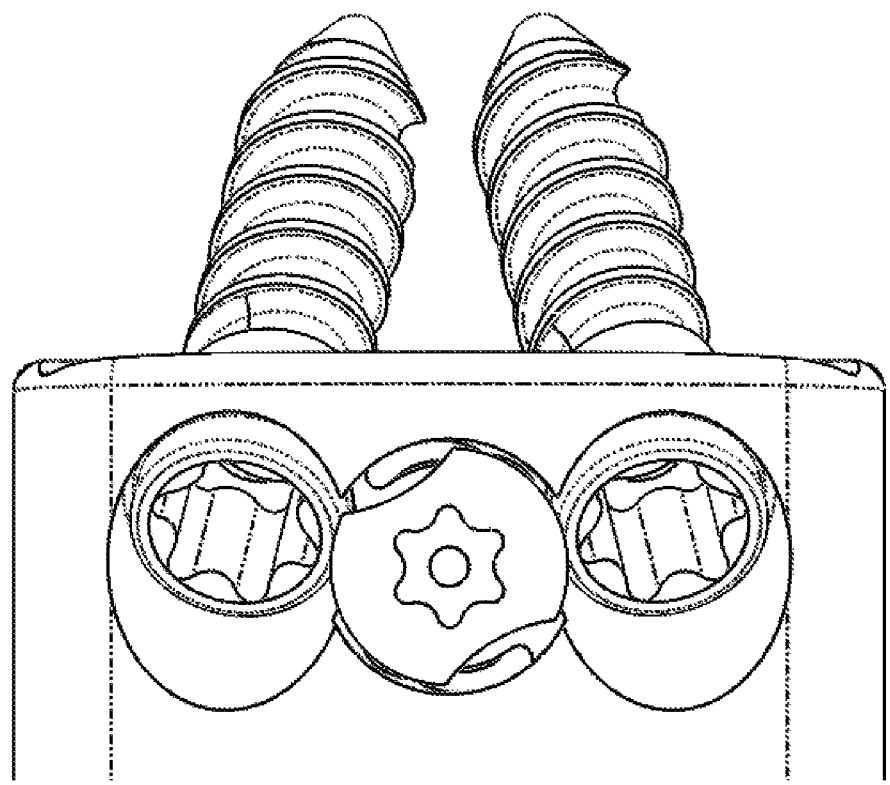
FIG. 9A is an enlarged front view of locking mechanism shown in FIG. 4.
Figure 9B:
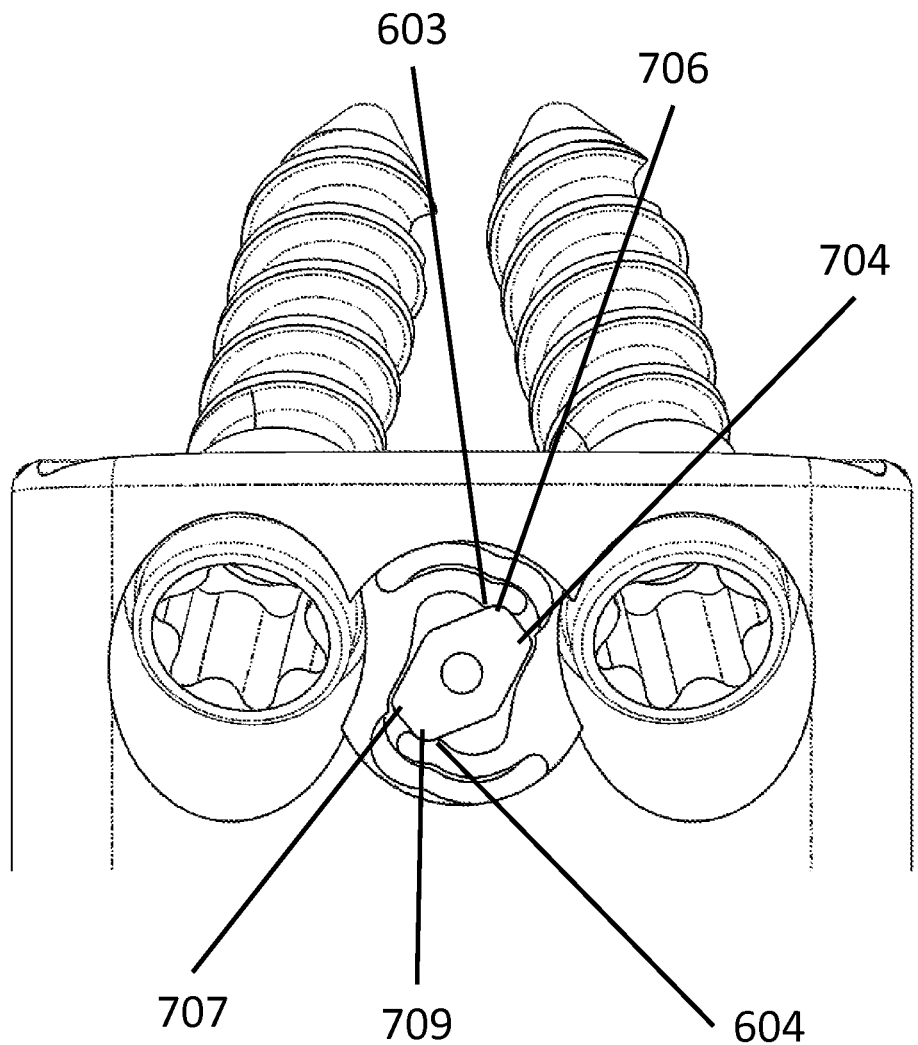
FIG. 9B is the enlarged front view of the locking mechanism shown in FIG. 9A without the cover piece of the locking mechanism.

FIG. 9A is shows locking mechanism 101 in corpectomy cage 100 in the locked position. Because retaining levers 601 and 602 have some limited flexibility, rotation of the engagement body 702 in the clockwise direction with the application of a force, will allow the retaining levers 601 and 602 to move radially outward to allow engagement body 702 to rotate from the position shown in FIG. 8B to the position shown in FIG. 9B. During such clockwise rotation, sides 704-706 rotate past indent 603 of retaining lever 601, such that side 706 is now to the immediate right of indent 603. This then precludes engagement body 702 from being able to rotate back counter-clockwise to the position shown in FIG. 8B. Likewise, sides 707-709 rotate past indent 604 of retaining lever 602, such that side 709 is now to the immediate left of indent 604. This then also precludes engagement body 702 from being able to rotate back counter-clockwise to the position shown in FIG. 8B. Thus, the engagement between the engagement body 702 and retaining levers 601 and 602 prevents engagement body 702 (and thus locking mechanism 101) from rotating clockwise into the locked position.

Furthermore, walls 801 and 802 are positioned such that this stops engagement body from turning further clockwise, i.e., walls 801 and 802 prevent over-rotation of engagement body 702. Accordingly, the practitioner cannot over-rotate when moving from the unlocked to the locked position.

When the locking mechanism is in the locked position, an application of force in the counter-clockwise direction will allow retaining levers 601 and 602 to expand radially, which then permits the engagement body 702 (and thus the locking mechanism 101) to return to the unlocked position shown in FIG. 8A-8B. Again, this cannot be over-rotated due to the walls 801 and 802.

Figure 10A:
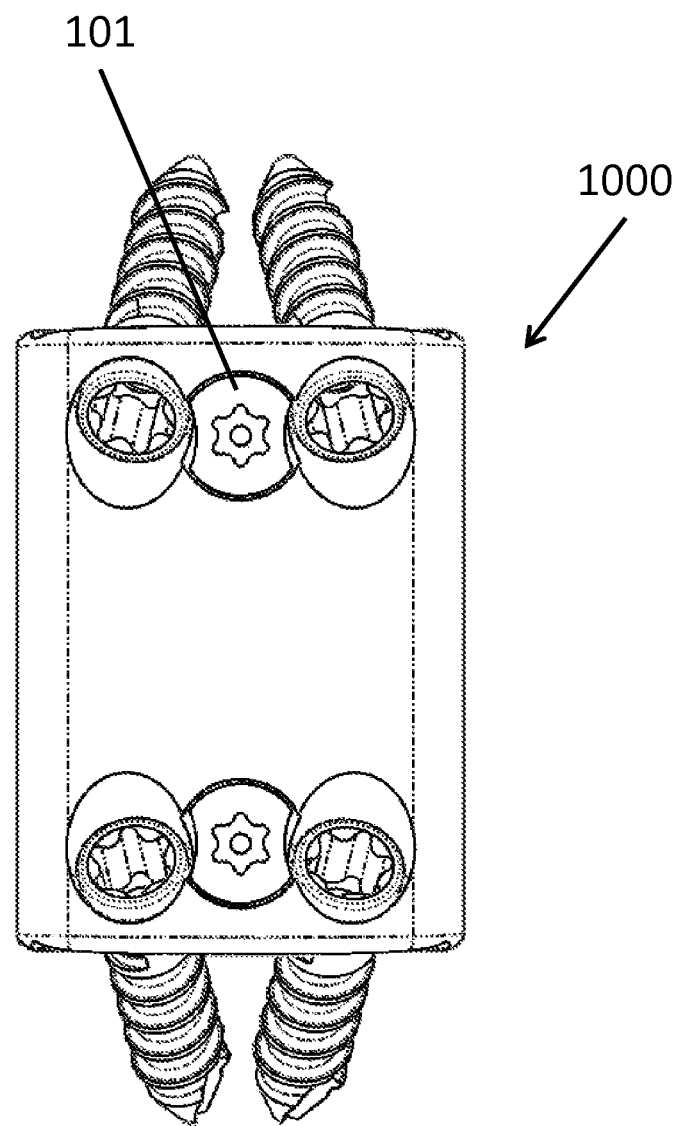
FIG. 10A is a front view of another embodiment of the present invention showing a single-part corpectomy cage with the locking mechanism in the unlocked position.
Figure 10B:
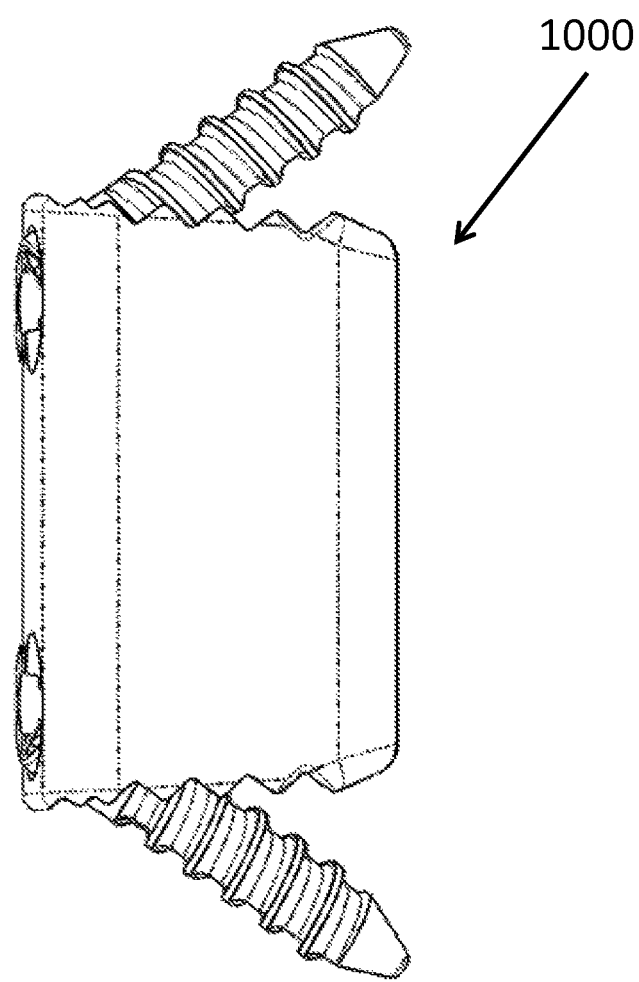
FIG. 10B is a right view of the embodiment of FIG. 10A.

FIG. 10A is a front view of a single-part corpectomy cage 1000 with the locking mechanism 101 in the unlocked position. FIG. 10B is a right view of the embodiment of single-part corpectomy cage 1000. FIG. 10B shows single-part corpectomy cage 1000 in one part, which can be made from a biocompatible material, such as titanium.

Figure 11A:
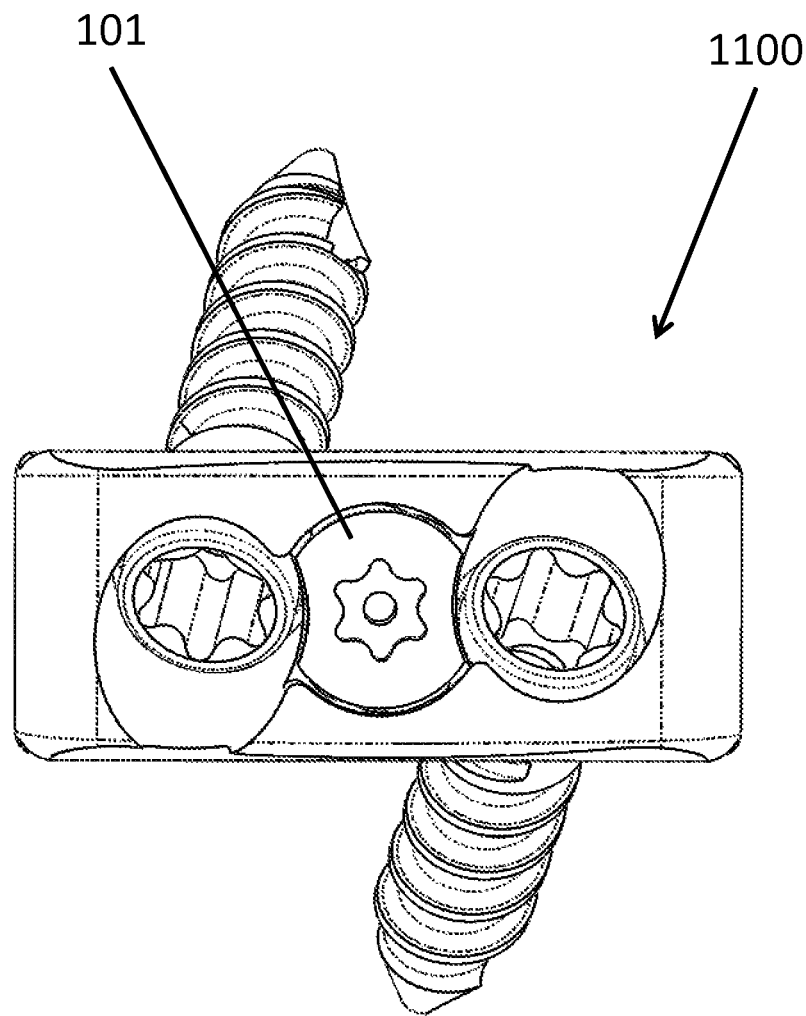
FIG. 11A is a front view of another embodiment of the present invention showing a single-part cervical cage with the locking mechanism in the unlocked position.
Figure 11B:
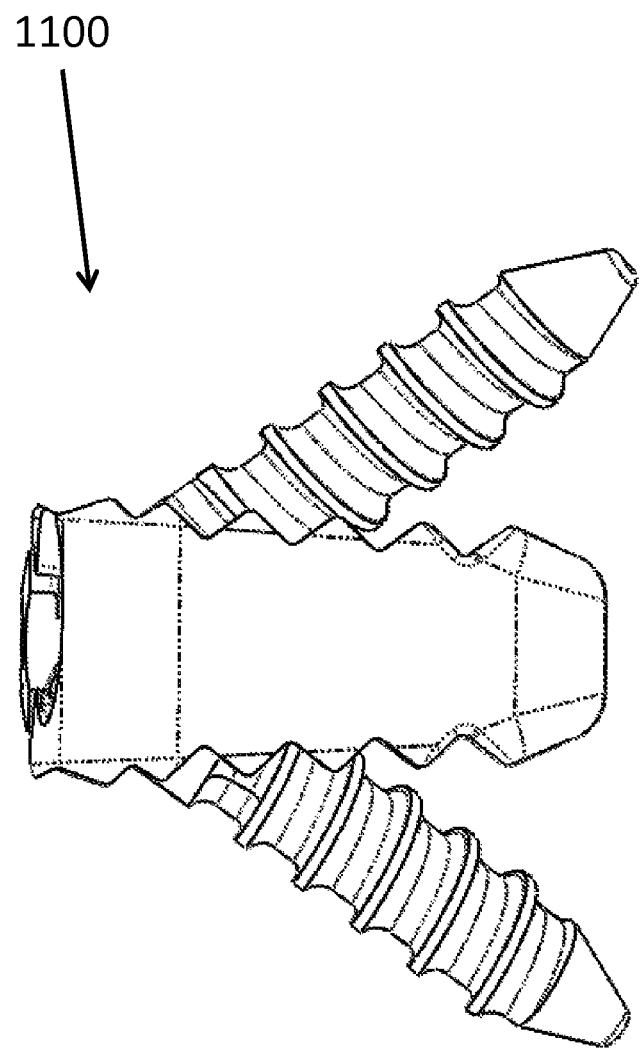
FIG. 11B is a right view of the embodiment of FIG. 11A.
Figure 11C:
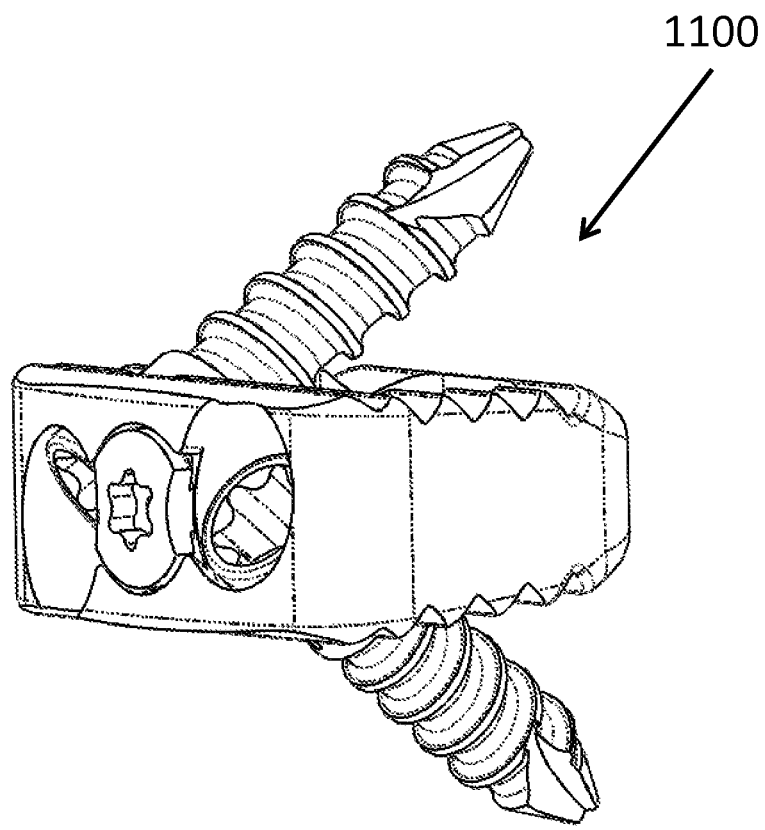
FIG. 11C is a perspective view of the embodiment of FIG. 11A.
Figure 11D:
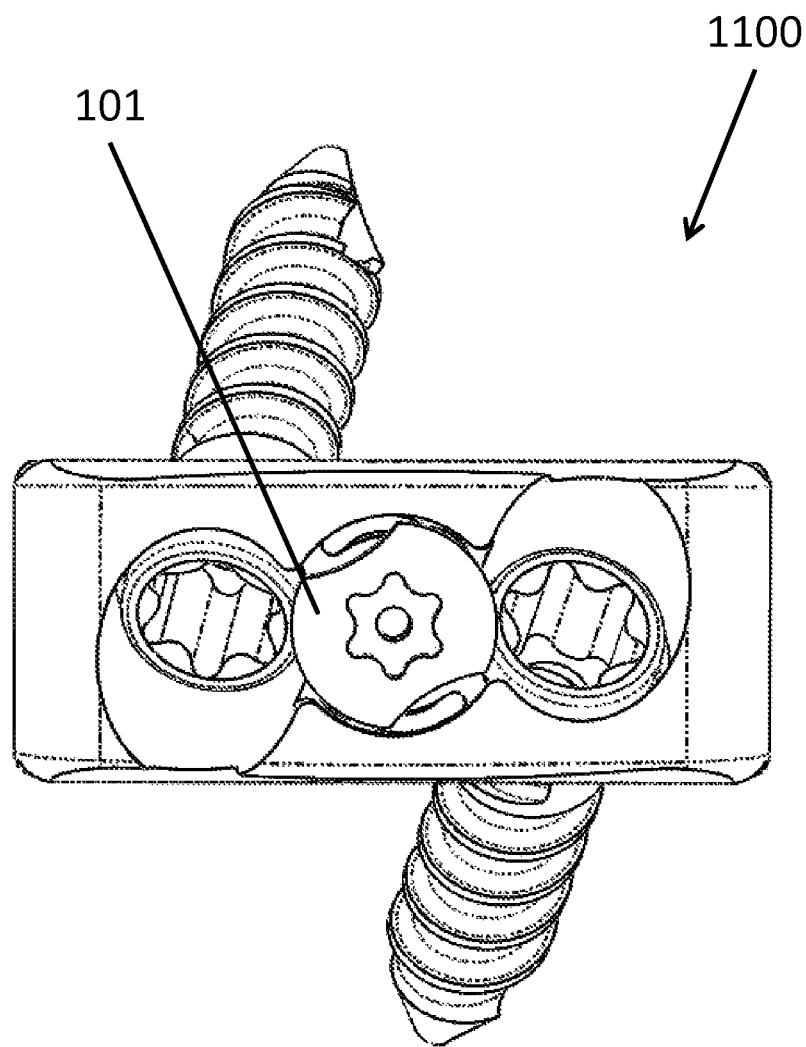
FIG. 11D is a front view of the embodiment of FIG. 11A with the locking mechanism in the locked position.

FIG. 11A is a front view of a single-part cervical cage 1100 with the locking mechanism 101 in the unlocked position. FIG. 11B-11C are, respectively, a right view and perspective view of single-part cervical cage 1100. FIG. 11D is a front view of single-part cervical cage 1100 with the locking mechanism 101 in the locked position.

Figure 12A:
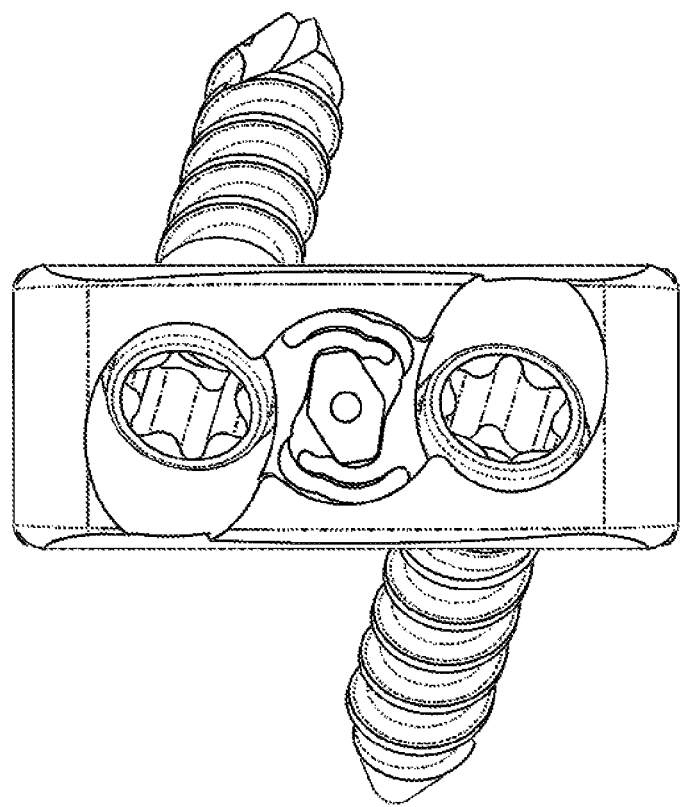
FIG. 12A is the front view of the embodiment of FIG. 11A without the cover piece of the locking mechanism.
Figure 12B:
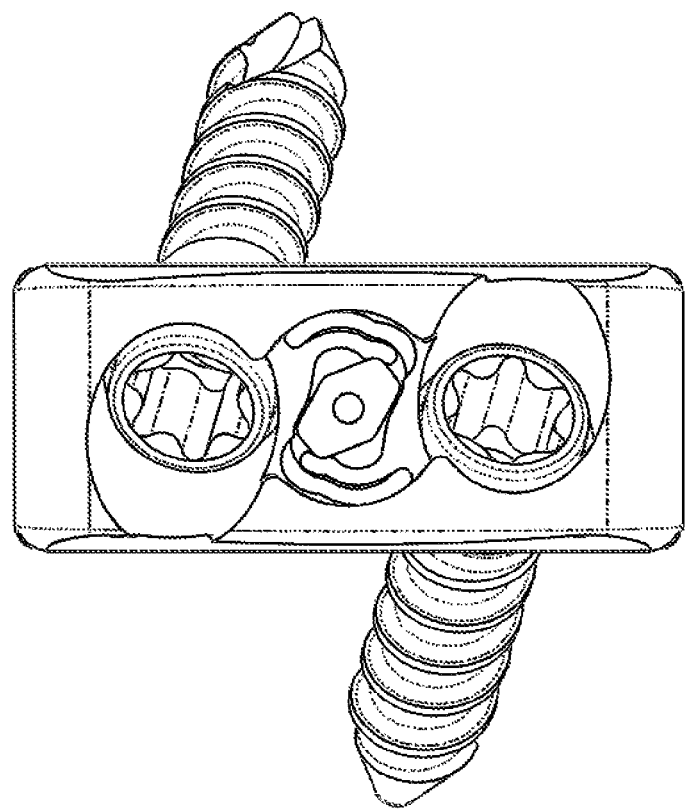
FIG. 12B is the front view of the embodiment of FIG. 11D without the cover piece of the locking mechanism.

FIG. 12A is the front view of single-part cervical cage 1100 without the cover piece 701 of the locking mechanism 101. FIG. 12B is the front view of single-part cervical cage 1100 without the cover piece 701 of the locking mechanism 101.

Figure 13A:
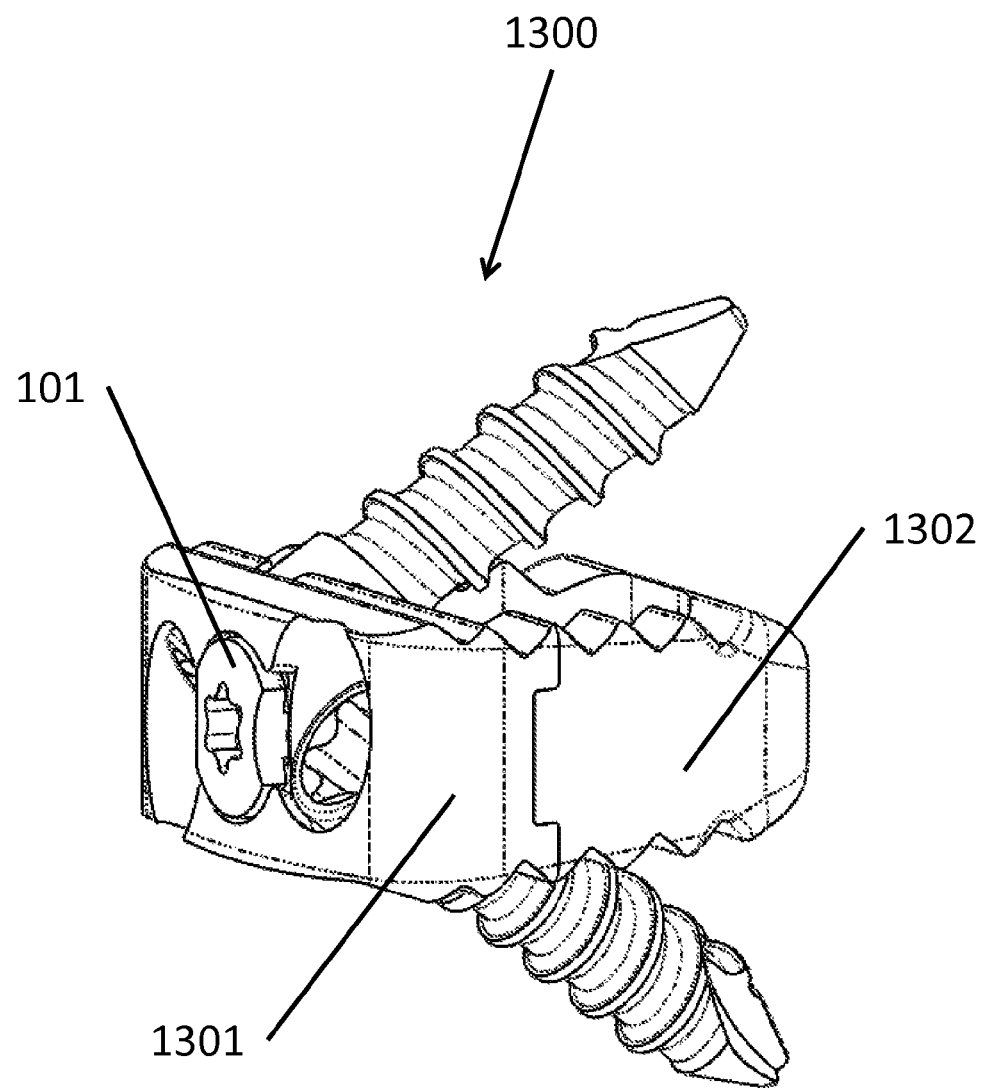
FIG. 13A is a perspective view of another embodiment of the present invention showing a two-part cervical cage with the locking mechanism in the unlocked position.
Figure 13B:
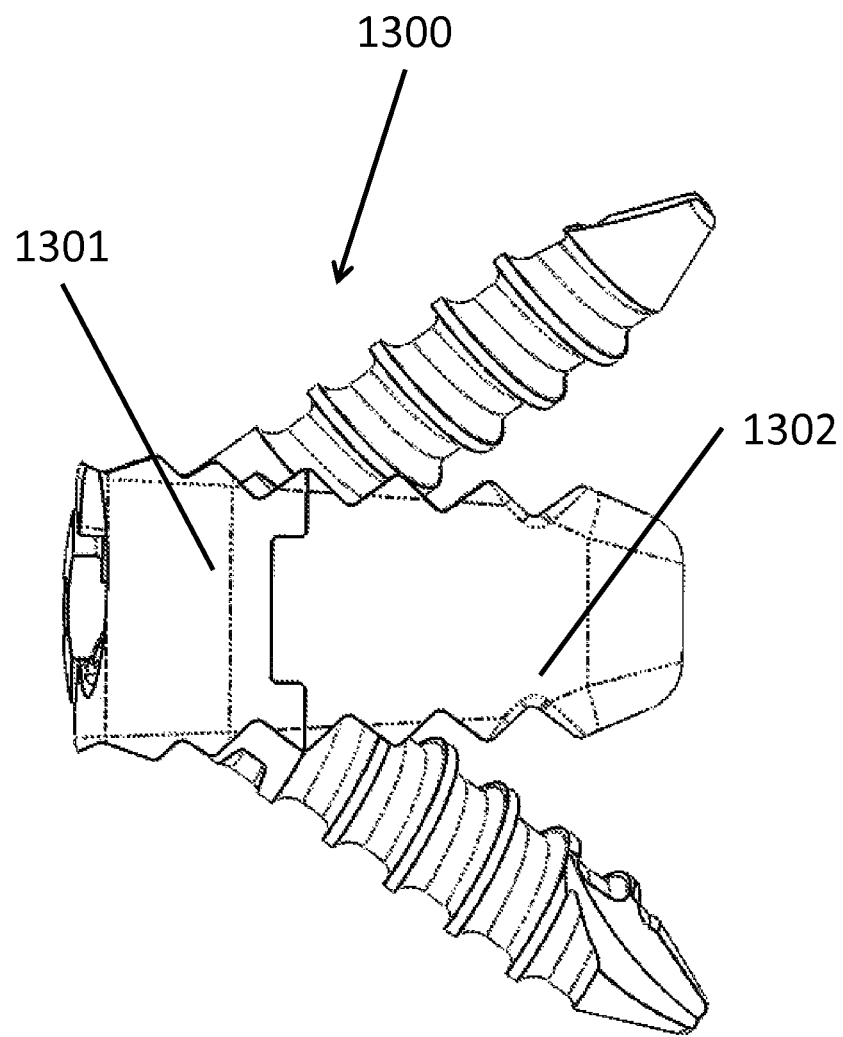
FIG. 13B is a right view of the embodiment of FIG. 13A.
Figure 14:
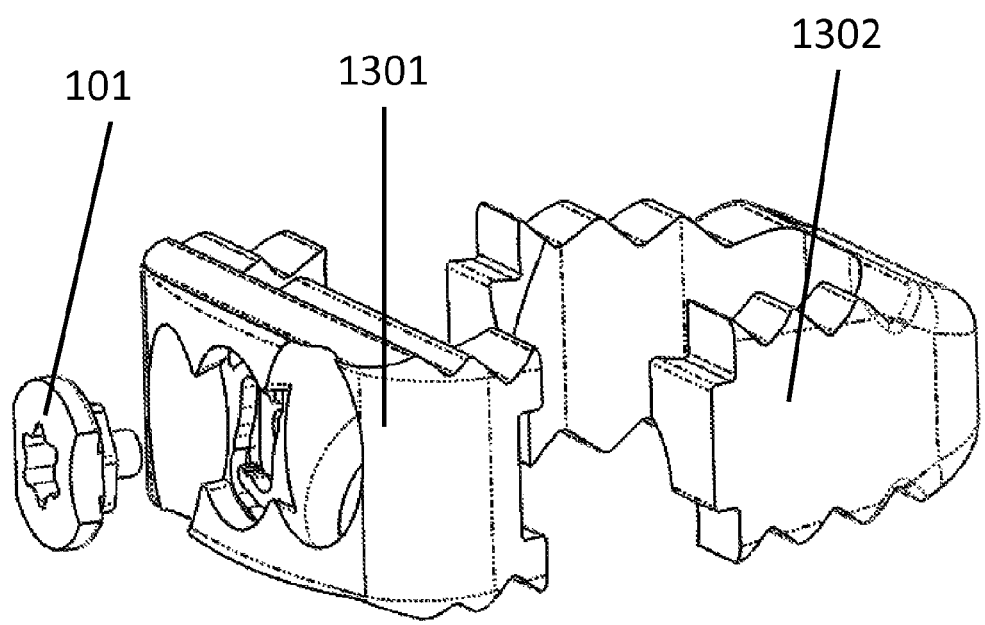
FIG. 14 is an exploded view of the embodiment of FIG. 13A.

FIG. 13A is a perspective view of a two-part cervical cage 1300 with the locking mechanism 100 in the unlocked position. FIG. 13B is a right view of two-part cervical cage 1300. FIG. 14 is an exploded view of two-part cervical cage 1300. FIGS. 13A-13B and 14 shows upper part 1301 and lower part 1302, which can be made from a biocompatible material. For instance, upper part 1301 can be made of titanium, and lower part 1302 can be made from PEEK or another biocompatible polymer.

The locking mechanism used in combination with the retaining mechanism in the corpectomy cages and cervical cages has significant advantageous. It provides for hard stops when moving between the open and closed positions. It also precludes over-rotation by the practitioner when implanting the corpectomy cage/cervical cage. Moreover, once the locking mechanism is set in place, locked or unlocked, it will be maintained in that position. The locking mechanism maintains its low profile because the retaining mechanism is able to fit in the space beneath it.

The disclosures of all patents, patent applications, and publications cited herein are hereby incorporated herein by reference in their entirety, to the extent that they provide exemplary, procedural, or other details supplementary to those set forth herein. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above.

What is claimed is:

1. A medical implant comprising:
   (a) a receiving member body that comprises a first fastener opening, wherein the first fastener opening is operable for allowing a first fastener to be inserted through the first fastener opening for fixing the medical implant to bone;
   (b) a locking mechanism located near the first fastener opening, wherein
      (i) the locking mechanism comprises a rotating block cover operable to move between an unlocked position and a locked position,
      (ii) when the rotating block cover is in the unlocked position, the first fastener can be inserted through the first fastening opening,
      (iii) when the rotating block cover is in the locked position, a portion of the rotating block cover is covering the first fastener opening to prevent the first fastener for moving through the first fastener opening and which locks the first fastener in place;
   (c) a retaining mechanism that comprises an engagement body rotatably coupled to at least two retaining levers, wherein
      (i) the engagement body is attached to the rotating block cover,
      (ii) the engagement body is operable for moving rotatably relative to the retaining levers while remaining in contact with the retaining levers,
      (iii) the engagement body is operable for moving in a first direction to a first position, wherein
         (A) when the engagement body is in the first position, the locking mechanism is in the unlocked position,
         (B) the engagement body is blocked from rotating past the first position when moved in the first direction, and
         (C) the engagement body is retained in the first position by the application of opposing rotational forces by the retaining levers such that the engagement body cannot move without the application of a force in a second direction that is opposite to the first direction, and
      (iv) the engagement body is operable for moving in a second direction to a second position, wherein
         (A) when the engagement body is in the second position, the locking mechanism is in the locked position,
         (B) the engagement body is blocked from rotating past the second position when moved in the second direction, and
         (C) the engagement body is retained in the second position by the application of opposing rotational forces by the retaining levers such that the engagement body cannot move without the application of a force in the first direction; and
   (d) wherein the medical implant is a cage.

2. The medical implant of claim 1, wherein the medical implant is a corpectomy cage.

3. The medical implant of claim 1, wherein the medical implant is a cervical cage.

4. The medical implant of claim 1, wherein
   (a) the medical device further comprises a second fastener opening,
   (b) the second fastener opening is operable for allowing a second fastener to be inserted through the second fastener opening for fixing the medical implant to bone,
   (c) the locking mechanism is further located near the second fastener opening,
   (d) when the rotating block cover is in the unlocked position, the second fastener can be inserted through the second fastening opening, and
   (e) when the rotating block cover is in the locked position, a portion of the rotating block cover is covering the second fastener opening to prevent the second fastener for moving through the second fastener opening and which locks the second fastener in place.

5. The medical implant of claim 1, wherein the first fastener comprises a bone screw.

6. The medical implant of claim 1, wherein the retaining mechanism comprises exactly two retaining levers.

7. The medical implant of claim 1, wherein each of the retaining levels has an indent that retains the engagement body in the first position and the second position.

8. The medical implant of claim 1, wherein the rotating block cover has a hole operable for receiving a rotatable tool, wherein the rotating block cover is rotatable in the first direction and the second direction using the rotating tool.

9. The medical implant of claim 1, wherein
   (a) the receiving member body comprises a plurality of fastener openings and plurality of locking mechanisms, and (b) each of the locking mechanisms is operable for locking fasteners positioned in at most two of the fastener openings.

10. The medical implant of claim 1, wherein the medical implant is a single-part medical implant.

11. The medical implant of claim 10, wherein the single part comprises titanium.

12. The medical implant of claim 1, wherein in the medical implant is a two-part medical implant comprising a first part and a second part.

13. The medical implant of claim 12, wherein
(a) the first part comprises titanium, and
(b) the second part comprises a biocompatible polymer.

14. The medical implant of claim 13, wherein the biocompatible polymer is polyether ether ketone (PEEK).

15. A method comprising:
(a) selecting a medical implant having a receiving body that comprises a first fastener opening, a locking mechanism, and a retaining mechanism, wherein
    (i) the locking mechanism comprises a rotating block cover operable to move between an unlocked position and a locked position,
    (ii) the locking mechanism is in the unlocked position,
    (iii) the retaining mechanism comprises an engagement body rotatably coupled to at least two retaining levers,
    (iv) the engagement body is attached to the rotating block cover,
    (v) the retaining mechanism retains the engagement body at a first position to maintain the rotating block cover in the unlocked position, wherein the at least two retaining levers apply opposing rotational forces to maintain the rotating block cover in the unlocked position, and
    (vi) the medical implant is a cage;
(b) inserting a first fastener into the first fastener opening;
(c) securing the first fastener to a bone;
(d) rotating the locking mechanism from the unlocked position to the locked position, wherein
    (i) a portion of the rotating block cover is covering the first fastener opening to prevent the first fastener for moving through the first fastener opening and which locks the first fastener in place,
    (ii) the engagement body is blocked from rotating to prevent the rotating lock cover from rotating past the locked position, and
    (iii) the retaining mechanism retains the engagement body at a second position to maintain the rotating block cover in the locked position wherein the at least two retaining levers apply opposing rotational forces to maintain the rotating block cover in the locked position.

16. The method of claim 15, wherein the medical implant is a corpectomy cage.

17. The method of claim 15, wherein the medical implant is a cervical cage.

18. The method of claim 15, wherein
(a) the medical implant further comprises a second fastener opening,
(b) the method further comprises (i) inserting a second fastener into the second fastener opening and (ii) securing the second fastener to the bone while the locking mechanism is in the unlocked position, and
(c) the step of rotating the locking mechanism further comprises that a portion of the rotating block cover is covering the second fastener opening to prevent the second fastener for moving through the second fastener opening and which locks the second fastener in place.

19. The method of claim 15, wherein the first fastener comprises a bone screw.

20. The method of claim 15, wherein the retaining mechanism comprises exactly two retaining levers.

21. The method claim 15, wherein the step of rotating the locking mechanism comprises inserting a rotating tool into a hole in the rotating block cover and rotating the rotating tool.

22. The method of claim 15, wherein
(a) the receiving member body comprises a plurality of fastener openings and plurality of locking mechanisms,
(b) the method comprises moving each of the locking mechanisms in the plurality of locking mechanism to lock at most two fasteners positioned in at most two fastener openings.

23. The method of claim 15, wherein the medical implant is a single-part medical implant.

24. The method of claim 23, wherein the single part comprises titanium.

25. The method of claim 15, wherein in the medical implant is a two-part medical implant comprising a first part and a second part.

26. The method of claim 25, wherein
(a) the first part comprises titanium, and
(b) the second part comprises a biocompatible polymer.

27. The method of claim 15 further comprising rotating the locking mechanism from the locked position to the unlocked position, wherein
(a) no portion of the rotating block cover is covering the first fastener opening which unlocks the first fastener,
(b) the engagement body is blocked from rotating to prevent the rotating lock cover from rotating past the unlocked position, and
(c) the retaining mechanism retains the engagement body at the first position to maintain the rotating block cover in the unlocked position, wherein the at least two retaining levers apply opposing rotational forces to maintain the rotating block cover in the unlocked position.

28. A The method comprising:
(a) selecting a medical implant having a receiving body that comprises a first fastener opening, a locking mechanism, and a retaining mechanism, wherein
    (i) the locking mechanism comprises a rotating block cover operable to move between an unlocked position and a locked position,
    (ii) the locking mechanism is in the unlocked position,
    (iii) the retaining mechanism comprises an engagement body rotatably coupled to at least two retaining levers,
    (iv) the engagement body is attached to the rotating block cover,
    (v) the retaining mechanism retains the engagement body at a first position to maintain the rotating block cover in the unlocked position, and
    (vi) the medical implant is a cage;
(b) inserting a first fastener into the first fastener opening;
(c) securing the first fastener to a bone;
(d) rotating the locking mechanism from the unlocked position to the locked position, wherein
    (i) a portion of the rotating block cover is covering the first fastener opening to prevent the first fastener for moving through the first fastener opening and which locks the first fastener in place,
    (ii) the engagement body is blocked from rotating to prevent the rotating lock cover from rotating past the locked position,
    (iii) the retaining mechanism retains the engagement body at a second position to maintain the rotating block cover in the locked position, and (iv) each of the retaining levers has an indent that retains the engagement body in the first position and the second position.

* * * * *